United States Patent [19]
Vucinovich

[11] Patent Number: 5,988,001
[45] Date of Patent: Nov. 23, 1999

[54] METHOD OF LOCATING A PARTICLE ON A SURFACE

[76] Inventor: Craig Vucinovich, 61 Orion Road, Kensington, Johannesburg, South Africa

[21] Appl. No.: 08/946,856

[22] Filed: Oct. 8, 1997

[30] Foreign Application Priority Data

Oct. 8, 1996 [ZA] South Africa ............................ 96/8473

[51] Int. Cl.⁶ ...................................................... G01N 1/04
[52] U.S. Cl. ...................................... 73/864.71; 73/863.21
[58] Field of Search .................................. 73/821, 865.5, 73/432.1, 864.71, 863.21; 422/68.1

[56] References Cited

U.S. PATENT DOCUMENTS

| | | | |
|---|---|---|---|
| 3,919,042 | 11/1975 | Spiller | 162/175 |
| 5,039,487 | 8/1991 | Smith | 422/56 |
| 5,243,864 | 9/1993 | Duummyre et al. | 73/864.71 |

FOREIGN PATENT DOCUMENTS

| | | |
|---|---|---|
| 2 302 540 | 9/1976 | France . |
| 57-125340 | 8/1982 | Japan . |
| 1599703 | 10/1990 | U.S.S.R. . |

*Primary Examiner*—Max Norri
*Attorney, Agent, or Firm*—Oblon, Spivak, McClelland, Maier & Neustadt, P.C.

[57] ABSTRACT

A method of locating a single particle on a target surface includes the steps of providing, on the target surface, a droplet of a liquid capable of wetting the surface of the particle, causing the particle to come into contact with the liquid, and allowing the liquid to evaporate. The method has particular application to the testing of the strength of a diamond and other abrasive particles.

11 Claims, 1 Drawing Sheet

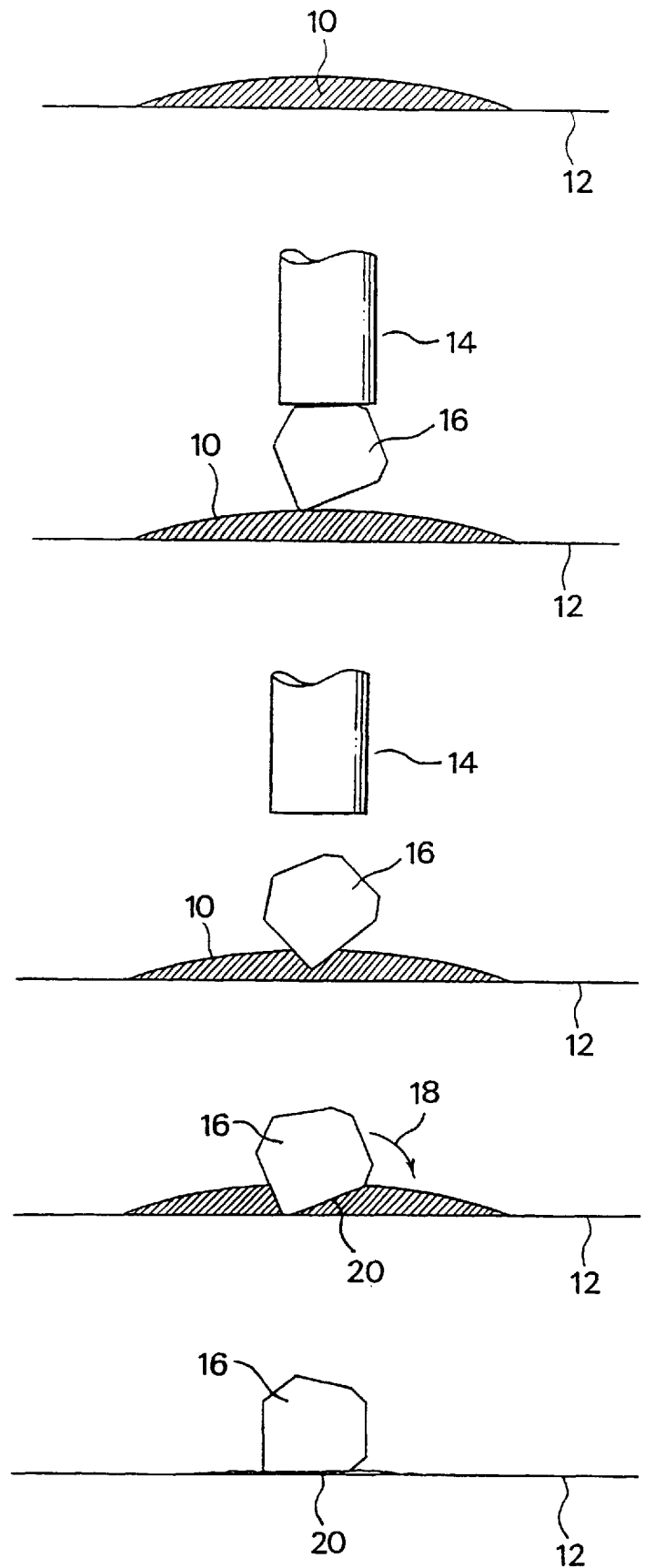

METHOD OF LOCATING A PARTICLE ON A
SURFACE

BACKGROUND OF THE INVENTION

This invention relates to a method of locating a particle on a surface. For quality control and also research purposes, it is necessary to be able to evaluate the strength of a particle such as a diamond particle. A crushing machine is used for this purpose. In use, the particle to be tested is placed between opposed anvils, the anvils brought together and a load applied. The particle will fracture and crush at a given load and from the data derived therefrom the strength of the particle can be determined.

It is important in the practical operation of a machine of this nature that a single particle be accurately placed between the anvils. This may be achieved by use of a vacuum needle which picks up a sample from a source of the particles. Vacuum needles rarely pick up a single particle alone. The extra, unwanted particles may be removed by repeating the process of vibrating the needle and then passing the needle carefully over a prepared brush which physically removes stubborn particles.

The needle, now carrying the single particle, is moved to a target area where the vacuum is released. However, owing to the electrical or mechanical attraction between the particle and the needle the particle remains attached to the needle. A small jet of air may be used to dislodge the particle but this usually results in the particle bouncing away from the target area. A further problem with this method is that the positioning of the particle on the target area is random. The particle can end up on an edge or a flat surface, or a point and will not always be centrally located in the target area. This can affect the results which are obtained.

SUMMARY OF THE INVENTION

According to the present invention, a method of locating a particle on a target surface includes the steps of providing, on the target surface, a liquid capable of wetting the surface of the particle, causing the particle to come into contact with the liquid, and allowing the liquid to evaporate.

The liquid on the target surface will typically be in the form of a droplet, layer or film. The particle may be brought close to the liquid and the force of attraction between the particle and liquid causing or resulting in the particle then coming into contact with the liquid.

BRIEF DESCRIPTION OF THE DRAWINGS

The drawing illustrates schematically the various steps in an embodiment of the method of the invention.

DESCRIPTION OF EMBODIMENTS

The method of the invention has application, in particular, to the locating of an abrasive particle, particularly a diamond particle, on a target surface for a strength test apparatus. It has been found that the liquid locates the particle positively. Further, the particle is influenced by the surface tension of the liquid which pulls it down on to the surface as the liquid evaporates. This tends to result in a flat region of the surface of the particle coming to rest on the target surface. Yet a further consequence and advantage of the method of the invention is that for small particles, e.g. a less than 1 mm and typically in the range 200 to 600 mm, the droplet exerts an attractive force which assists in dislodging the particle from its captive position, e.g. on a vacuum needle.

The liquid must have the ability to wet the surface of the particle and evaporate, generally under ambient conditions. In the case of diamond particles, examples of suitable liquids are aliphatic alcohols, particularly methanol.

An embodiment of the invention will now be described with reference to the accompanying drawings. A low vacuum, high air-flow carrying hypodermic needle was lowered into a sample bowl containing a mass of diamond particles, for example, SDA particles, and picked up a particle(s) on the needle tip as it was retracted. Ideally, only one particle is selected, but normally more than one particle adheres to the needle tip.

As the vacuum needle reached the end of its vertical stroke, it was rapidly decelerated and then rapidly accelerated on its horizontal stroke. This caused the relatively long needle to vibrate and displace any particles not directly in an air stream passing across the needle. The vacuum needle was then passed over a carefully selected and prepared brush which physically removed stubborn particles unaffected by the vibratory dislodgement.

A second hypodermic needle was used to deliver a small droplet 10, typically 0,5 μl, of methanol on to a target surface 12. Methanol is an active diamond wetting agent.

The vacuum needle 14 and the accompanying single particle 16 were then placed vertically above the methanol droplet 10 and the vacuum released.

If the particle is dislodged from the needle it falls into and is retained by the methanol droplet. If the particle remains attached the vacuum needle, the particle is brought into the vicinity of the methanol drop and may be allowed to touch the methanol droplet. The attraction between the droplet 10 and the particle 16 results in the particle being dislodged and falling into the droplet, where it is retained. As the methanol evaporated, the droplet 10 reduced in size and the surface tension caused the particle to move in the direction of the arrow 18. The end result was that the particle was so located on the target surface 12 that a flat surface 20 thereof came to rest on, and in contact with, this surface. This is a stable position for the particle and also a desirable one for a strength test to be performed on the particle.

The target surface may have an adhesive coating to ensure that the particle remains in position.

The embodiment described above uses a droplet to capture the particle. A layer or film of the liquid may be used as an alternative. The liquid layer or film may be applied to the target surface by a felt-tipped applicator, for example.

I claim:

1. A method of locating a single particle on a target surface includes the steps of:

providing, on the target surface, a droplet of liquid capable of wetting the surface of the particle;

causing the particle to come into contact with the droplet of liquid; and allowing the droplet of liquid to evaporate.

2. A method according to claim 1 wherein the liquid is an aliphatic alcohol.

3. A method according to claim 1 wherein the droplet of liquid on the target surface is in the form of a layer or film.

4. A method according to claim 1 wherein the single particle is brought close to the droplet of liquid and the force of attraction between the liquid and the particle causes the single particle to come into contact with the droplet of liquid.

5. A method according to claim 1 wherein the single particle has a flat region and that flat region comes to rest on the target surface after the droplet of liquid is allowed to evaporate.

6. A method according to claim 1 wherein the single particle has a size of less than 1 mm.

7. A method according to claim 1 wherein the particle has a size in the range of 200 to 600 $\mu$m.

8. A method according to claim 1 wherein the single particle is located on an end of a vacuum needle when it is caused to be brought into contact with the droplet of liquid.

9. A method according to claim 1 wherein the single particle is an abrasive particle.

10. A method according to claim 9 wherein the abrasive particle is a diamond particle.

11. A method according to claim 2 wherein the aliphatic alcohol is methanol.

* * * * *

UNITED STATES PATENT AND TRADEMARK OFFICE
CERTIFICATE OF CORRECTION

PATENT NO. : 5,988,001
DATED : NOVEMBER 23, 1999
INVENTOR(S) : CRAIG VUCINOVICH

Page 1 of 3

It is certified that error appears in the above-identified patent and that said Letters Patent is hereby corrected as shown below:

On the title page item [56], column, line 4, change "Duummyre" to --Dunmyre--;

line 9, change "Norri" to --Noori--; and line 13, after "single" insert --nonairborne--.

Column 1, between lines 5 and 6, insert "Field of the Invention";

line 6, after "a" (second occurrence), insert --nonairborne--;

line 7, after "surface.", start a new paragraph and insert "Description of Related Art";

line 27, after "needle" (first occurrence), insert a comma;

line 28, after "this" insert --action--;

line 34, after "This" insert --randomness--;

line 54, change "DESCRIPTION OF EMBODIMENTS" to --DETAILED DESCRIPTION OF PREFERRED EMBODIMENTS--;

line 62, after "This" insert --action--;

line 66, change "mm" to --µm--;

Column 2, line 24, change "0,5" to --0.5--;

line 26, change "The" to --A--; change "the" to --an--;

line 29, after "particle" insert --16--; after "needle" insert --14--;

UNITED STATES PATENT AND TRADEMARK OFFICE
CERTIFICATE OF CORRECTION

PATENT NO. : 5,988,001
DATED : NOVEMBER 23, 1999    Page 2 of 3
INVENTOR(S) : CRAIG VUCINOVICH

It is certified that error appears in the above-identified patent and that said Letters Patent is hereby corrected as shown below:

line 30, after "droplet" but before the period, insert --10--; after "particle" insert --16--;

line 31, after "needle" but before the comma, insert --14--; after "particle" insert --16--;

line 32, change "drop" to --droplet 10--;

line 33, after "droplet" (first occurrence) but before the period, insert --10--;

line 34, after "particle" (second occurrence) insert --16--;

line 35, after "droplet" but before the comma, insert --10--;

line 37, after "particle" insert --16--; change "the" (third occurrence) to --an--;

line 38, after "particle" insert --16--;

line 40, after "this" insert --flat--; after "surface" but before the period, insert "20"; after "This" insert --placement--;

line 41, after "particle" insert --16--;

line 42, after "particle" but before the period, insert --16--;

line 43, after "surface" insert --12--;

line 44, after "particle" insert --16--;

line 45, after "droplet" insert --10--;

UNITED STATES PATENT AND TRADEMARK OFFICE
CERTIFICATE OF CORRECTION

PATENT NO. : 5,988,001
DATED : NOVEMBER 23, 1999
INVENTOR(S) : CRAIG VUCINOVICH

It is certified that error appears in the above-identified patent and that said Letters Patent is hereby corrected as shown below:

line 46, after "particle" but before the period, insert --16--;

line 48, after "surface" insert --12--.

line 50, in claim 1, after "single", insert --nonairborne--;

line 51, in claim 1, change "includes" to --comprising--;

line 52, in claim 1, after "surface" but before the comma, insert --which is one for a strength test apparatus--.

Signed and Sealed this

Thirtieth Day of January, 2001

Attest:

Q. TODD DICKINSON

Attesting Officer       Director of Patents and Trademarks